United States Patent [19]
Crivellaro

[11] Patent Number: 5,387,179
[45] Date of Patent: Feb. 7, 1995

[54] MODIFIED ERECTION RING

[76] Inventor: Jurgen Crivellaro, Reinbeker Strabe 10 a, 2000 Stapelfeld, Germany

[21] Appl. No.: 776,288
[22] PCT Filed: Apr. 10, 1991
[86] PCT No.: PCT/EP91/00680
  § 371 Date: Feb. 6, 1992
  § 102(e) Date: Feb. 6, 1992
[87] PCT Pub. No.: WO91/15173
  PCT Pub. Date: Oct. 17, 1991

[30] Foreign Application Priority Data
  Apr. 10, 1990 [DE] Germany ............... 4138767

[51] Int. Cl.⁶ .................................. A61F 5/00
[52] U.S. Cl. ........................... 600/38; 600/39; 600/41
[58] Field of Search ............... 600/38, 39, 41; 446/15, 446/16

[56] References Cited
U.S. PATENT DOCUMENTS

| | | | |
|---|---|---|---|
| 2,382,949 | 8/1945 | McLaren | 446/15 |
| 2,928,205 | 3/1960 | Fulton | 446/15 |
| 4,440,183 | 4/1984 | Miller | 600/41 |

Primary Examiner—Randall L. Green
Assistant Examiner—Mary Beth Jones
Attorney, Agent, or Firm—Cushman, Darby & Cushman

[57] ABSTRACT

A sexual stimulation device for the male includes an erection ring from which extends a rectal rod; the device is made from a flexible plastic having a Shore hardness between approximately 30 and 60.

4 Claims, 1 Drawing Sheet

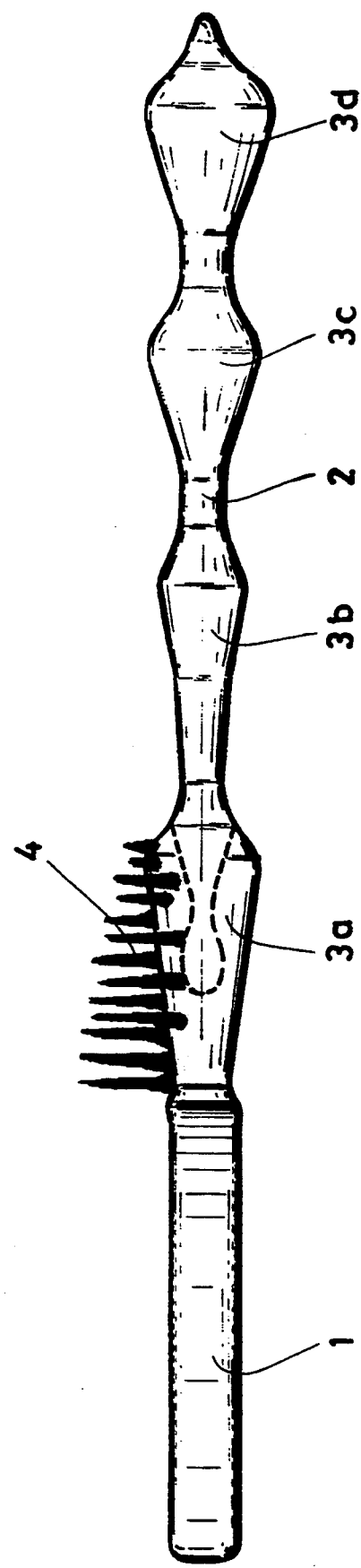

MODIFIED ERECTION RING

BACKGROUND OF THE INVENTION

1. Field of the Invention

The invention relates to a modified erection ring.

2. Description of Related Art

Penile rings, also called erection rings, have been in use for centuries in many cultures and are often employed to remedy impaired potency in men. Penile rings may be made of an elastic or non-elastic material such as rubber or, as in the Japanese cultural area, of porcelain or ivory and by means of a reduction of the return of blood in the arteries cause the generation or preservation of an erection.

In accordance with the findings of medical sexologists, potency difficulties in men are widely spread and appear to increase continuously, particularly with increasing age, and very often result in psychological and social problems. One reason for the increase appears to lie, for example, in the increased administration of beta blockers to combat heart and blood pressure symptoms in men starting approximately at the age of 40. Therefore the use of erection rings is also recommended by medical sexologists in case of impaired potency.

However, it has been shown that the use of such erection rings for the support of weak penile erections and for preservation of an erection are often insufficient. On the other hand it is known that the anal region and the rectum are sensitive and that a stimulation of this area can lead to a spontaneous and prolonged erection in many men.

SUMMARY OF THE INVENTION

The invention therefore proposes an erection ring which is characterized in that it forms a one-piece connection with a rectal rod. In this way a simultaneous stimulation of the sensory nerves in the anal region and the rectum as well as the conventional pressor effect of the penis ring is possible. In cases of psychologically caused impairment of potency, considerable success can be achieved by means of this combination, which results in a spontaneous and lasting erection.

BRIEF DESCRIPTION OF THE DRAWING

The invention will be described in detail below by means of the drawings.

DETAILED DESCRIPTION OF THE INVENTION

The drawing figure shows an erection ring in accordance with the invention in a top view. The erection ring 1 is connected in one piece with a rectal rod 2, which preferably has enlargements 3a, 3b, 3c and 3d of varied diameters for increasing the stimulation. The erection ring consists of physiologically harmless plastic materials and in particular of modified styrene-butadiene-styrene block copolymers, which are distinguished by great flexibility, high restoring capabilities and great static friction. The plastic materials used should have a Shore hardness between approximately 30 and 60, preferably around 40. The preferably used styrene-butadiene-styrene block copolymers are easily worked by means of all thermoplastic production methods and are particularly distinguished in that molding without the formation of mold marks is possible.

I claim:

1. A stimulation device comprising an erection ring having a rectal rod integral with and extending from said ring, said device being made from a plastic material that is physiologically harmless and has a Shore hardness of between approximately 30 and 60.

2. An erection ring in accordance with claim 1, characterized by enlargements (3a, 3b, 3c, 3d) of the rectal rod (2) with varying diameters.

3. An erection ring in accordance with claims 1, comprising a modified styrene-butadiene-styrene block copolymers.

4. The device as claimed in claim 1 wherein the Shore hardness if approximately 40.

* * * * *